(12) United States Patent
VanDusseldorp

(10) Patent No.: US 7,410,490 B2
(45) Date of Patent: Aug. 12, 2008

(54) SURGICAL DEVICE

(75) Inventor: Gregg A. VanDusseldorp, Crown Point, IN (US)

(73) Assignee: Omnitech Systems, Inc., Valparaiso, IN (US)

( * ) Notice: Subject to any disclaimer, the term of this patent is extended or adjusted under 35 U.S.C. 154(b) by 169 days.

(21) Appl. No.: 10/908,649

(22) Filed: May 20, 2005

(65) Prior Publication Data

US 2005/0222586 A1    Oct. 6, 2005

Related U.S. Application Data

(63) Continuation-in-part of application No. 10/604,297, filed on Jul. 9, 2003, which is a continuation-in-part of application No. 09/714,808, filed on Nov. 15, 2000, now Pat. No. 6,416,519.

(51) Int. Cl.
*A61B 17/22* (2006.01)
*A61B 17/26* (2006.01)

(52) U.S. Cl. .................. 606/113; 606/205; 606/127

(58) Field of Classification Search .................. 606/113, 606/114, 200, 127, 128, 138, 205
See application file for complete search history.

(56) References Cited

U.S. PATENT DOCUMENTS 5,944,728 A * 8/1999 Bates .................. 606/127
6,183,482 B1 * 2/2001 Bates et al. .................. 606/127
6,416,519 B1 * 7/2002 VanDusseldorp .................. 606/127
6,500,182 B2   12/2002 Foster .................. 606/127
2002/0068954 A1   6/2002 Foster .................. 606/200

FOREIGN PATENT DOCUMENTS

DE    197 22 429 A1    3/1998
WO    WO 01/97699 A1   12/2001

* cited by examiner

*Primary Examiner*—Todd E. Manahan
*Assistant Examiner*—Amy T. Lang
(74) *Attorney, Agent, or Firm*—Hartman & Hartman, P.C.; Gary M. Hartman; Domenica N. S. Hartman

(57) ABSTRACT

A surgical device having a sheath and legs slidably received within the sheath. The legs are adapted to move outwardly away from each other when deployed from the sheath to establish a deployed position, and to move inwardly toward each other to collapse within the sheath and define a stowed or grasping position. Each of the legs has a transverse cross-sectional shape defined by a concave surface, an oppositely-disposed convex surface, and lateral sides interconnecting the concave and convex surfaces. The legs and sheath are configured to cause the legs to fully collapse within the sheath such that the lateral sides of adjacent pairs of the legs contact each other, and/or the legs define a tubular shape having a circular opening defined by the concave surfaces of the legs and a circular exterior cross-section defined by the convex surfaces of the legs.

12 Claims, 5 Drawing Sheets

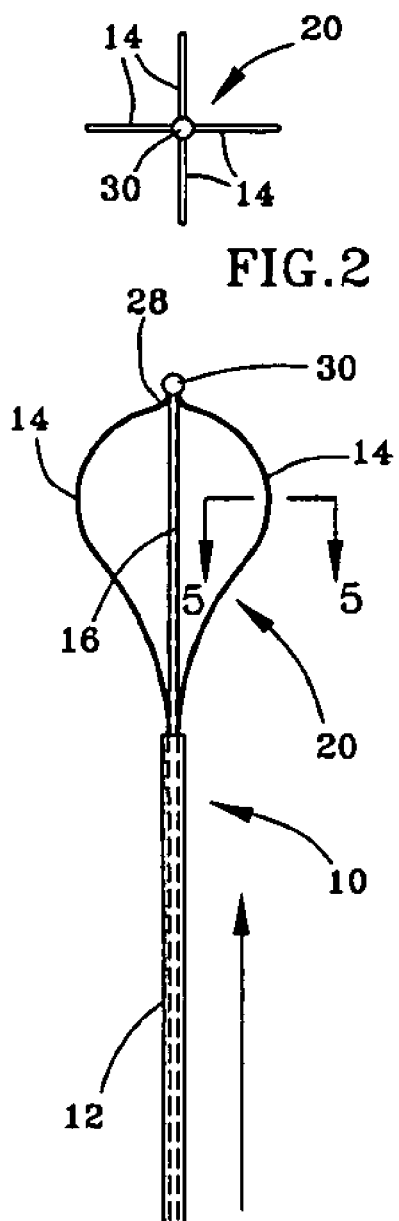
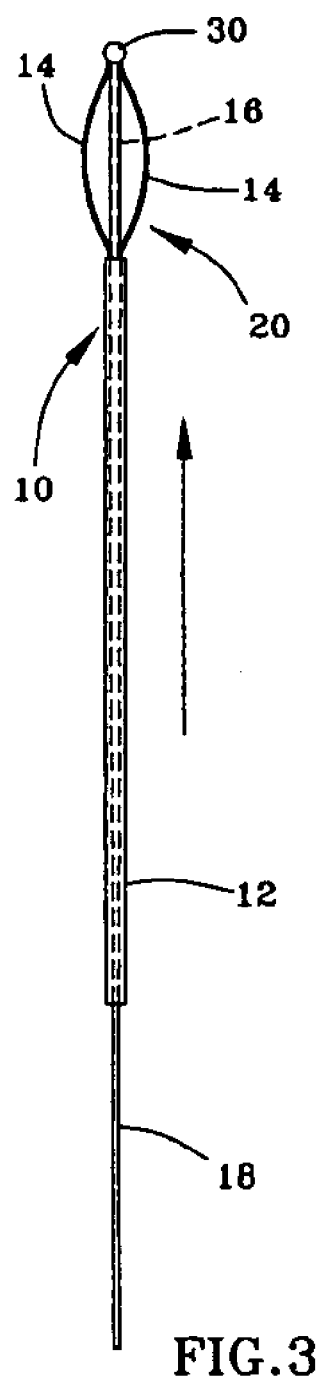
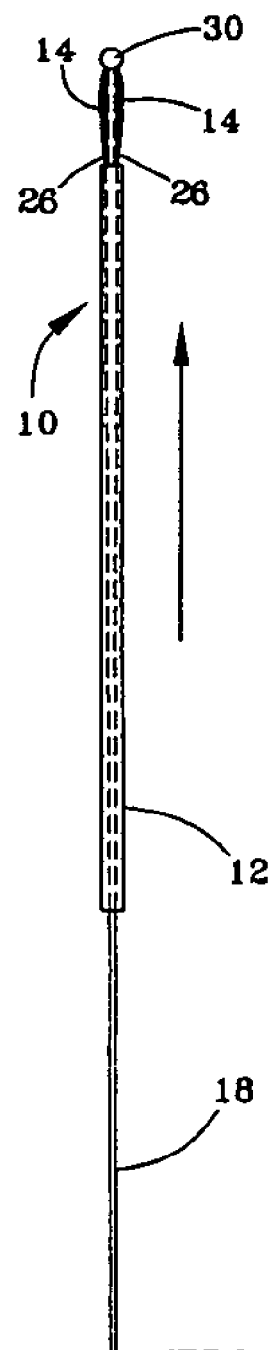
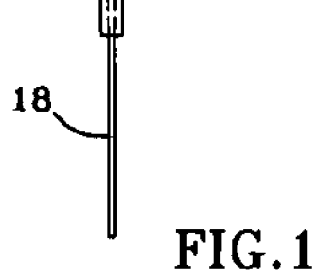
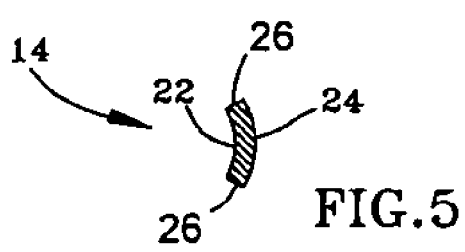

SURGICAL DEVICE

CROSS REFERENCE TO RELATED APPLICATIONS

This is a continuation-in-part patent application of U.S. patent application Ser. No. 10/604,297, filed Jul. 9, 2003, which is a continuation-in-part patent application of prior application Ser. No. 09/714,808 filed Nov. 15, 2000, now U.S. Pat. No. 6,416,519.

BACKGROUND OF THE INVENTION

The present invention generally relates to surgical devices adapted to capture an object within a cavity of the human body, such as when moving, manipulating and extracting biological material during a medical procedure. More particularly, this invention relates to a surgical device comprising elongate members that, when collapsed toward each other, are capable of capturing an object, and wherein each of the elongate members has a cross-sectional shape that promotes the ability of the elongate members to expand and collapse relative to the other members.

Various instruments are known in the art for surgically removing stones, calculi and other hard materials from the body. An example is an extraction instrument disclosed in U.S. Pat. No. 5,281,230 to Heidmueller as comprising a pair of bowls that are pivoted toward and away from each other by engaging their proximal ends with a sheath. Other types of extraction instruments make use of multiple wires that are flexed to grasp an object. For example, U.S. Pat. No. 5,944,728 to Bates discloses an instrument having arcuate wires with rectangular, round, D-shaped, or V-shaped cross-sections. The wires form a basket when a plunger associated with the instrument is in a distal position, allowing the legs to radially collapse toward each other. To expand the legs, the plunger must be actuated into engagement with the legs, forcing the legs radially apart from each other. As such, surgically moving, manipulating and extracting material from a body cavity is complicated by the requirement to additionally operate the plunger to expand and contract the legs.

Another example of an extraction instrument is disclosed in U.S. Pat. No. 6,203,552 to Bagley et al. As with Bates, the instrument taught by Bagley et al. has arcuate legs that form a collapsible basket when actuated with respect to a sheath. Each leg has a wedge-shaped cross-sectional shape, so that together they fill the cross-sectional area of the sheath. Contrary to Bates, the instrument disclosed by Bagley et al. does not require a separate plunger to expand (dilate) and collapse the basket.

U.S. Pat. No. 6,500,182 to Foster and U.S. Patent Application Publication No. 2002/00668954 to Foster disclose other extraction instruments configured to be actuated without the assistance of a plunger. Each instrument taught by Foster has resilient grasping members (legs) that form a basket or forceps when extended from a sheath, and which collapse toward each other when the sheath is advanced over the legs (or the legs are retracted into the sheath). According to Foster, the legs are formed by cutting or forming slots in an elongated cylindrical member, such as a cannula. If formed from a cannula, the legs are said to have semicircular cross-sectional shape. The edges of the legs are said to be spaced apart when in the compact (collapsed) position, a condition which appears to be inherent because each adjacent pair of legs is separated by the slot formed during the cutting/forming operation that defined the legs. As such, it appears the legs cannot be fully collapsed with the sheath, since the sheath cannot have an inner diameter smaller than the cannula from which the legs were defined and which must also be accommodated within the sheath.

There is an ongoing effort to devise surgical extraction instruments with greater dilating force when expanding to acquire an object, with greater grasping strength when capturing onto an object, and that maintain their form and alignment throughout their range of motion so as to more easily capture biological material during a variety of medical procedures.

BRIEF SUMMARY OF THE INVENTION

The present invention provides a surgical device having a sheath with an interior passage and legs slidably received within the passage of the sheath. The legs are adapted to move outwardly away from each other when deployed from the sheath to establish a deployed position, and to move inwardly toward each other to collapse within the sheath and define a stowed position. Each leg has a transverse cross-sectional shape defined by a first surface that is concave, an oppositely-disposed second surface that is convex, and lateral sides interconnecting the first and second surfaces.

According to one aspect of the invention, the legs and sheath are configured to cause the legs to fully collapse within the sheath such that the lateral sides of adjacent pairs of the legs contact each other, preferably along their entire lengths, when the legs are within the sheath. According to another aspect of the invention, when in the stowed position the legs are substantially parallel to each other and define a tubular shape having a circular opening defined by the first surfaces of the legs and a circular exterior cross-section defined by the second surfaces of the legs.

The legs have distal ends that may be connected together so that the legs define a basket in the deployed position, and so that the basket collapses as the sheath is advanced over the legs so as to define a grasping position in which the legs are operable to perform a grasping operation. Alternatively, the legs are not connected such that the device is operable as forceps. With each of these embodiments, each leg is preferably formed to have a parabolic curved shape, enabling the legs to automatically deploy radially outward and away from each other when outside the sheath, thereby eliminating the need for a plunger to expand the basket or forceps formed by the legs. The cross-sectional shape of the legs is capable of contributing greater strength and rigidity to the legs to promote their ability to expand with a sufficient force that eliminates the need for a plunger, to provide greater grasping strength when collapsed, and to maintain their form and alignment throughout their range of motion. Furthermore, because the legs are supported and arranged so that their lateral sides contact each other when the legs are fully within the sheath, the grasping strength of the legs is maximized when attempting to capture an object and thereafter complete containment is possible of very small objects such as renal or ureteral calculi. As a result, the device is capable of reliably moving, manipulating and extracting biological material in a variety of medical procedures.

Other objects and advantages of this invention will be better appreciated from the following detailed description.

BRIEF DESCRIPTION OF THE DRAWINGS

FIGS. 1 and 2 are side and end views, respectively, of a surgical device in a deployed position in accordance with a first embodiment of this invention.

FIGS. 3 and 4 are side views of the surgical device of FIG. 1 in intermediate and grasping positions, respectively.

FIG. 5 is a cross-section along line 5-5 of FIG. 1.

DETAILED DESCRIPTION OF THE INVENTION

Figure 6:
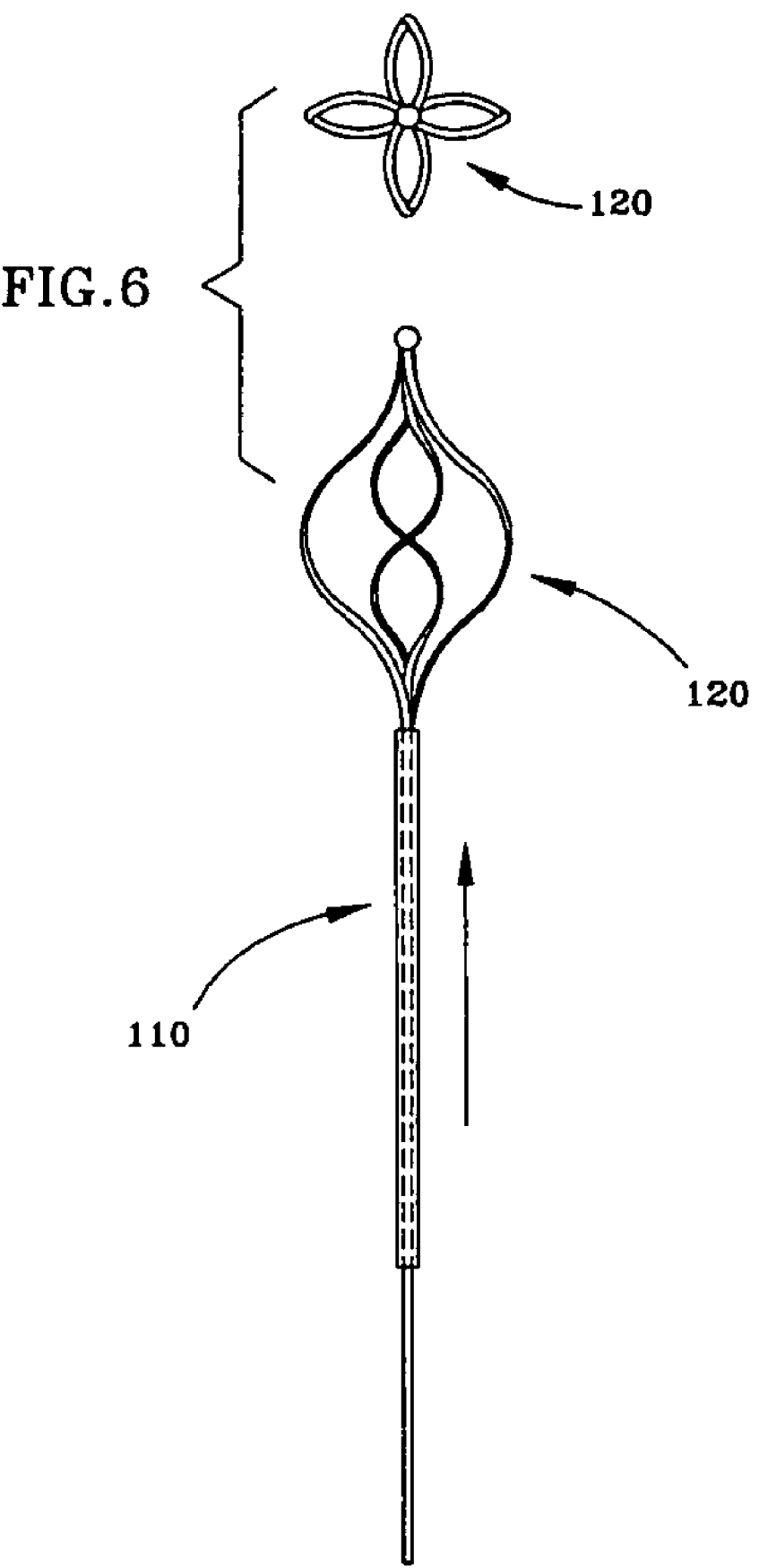
FIG. 6 shows a surgical device in accordance with a second embodiment of this invention.

With reference to FIGS. 1 through 4, a surgical device 10 is shown in accordance with a first embodiment of this invention. The device 10 is particularly intended and suitable for extraction procedures, in which biological materials are required to be surgically moved, manipulated and/or extracted from a cavity of the human body. As such, the device 10 can be adapted for use as, for example, a urological, gynecological, cardiological, laparoscopical, or gastrointestinal instrument.

The extraction device 10 is depicted as comprising a sheath 12, legs 14 that project from a passage within the sheath 12, and a cable 18 (or other suitable actuating member) for deploying the legs 14 from the sheath 12 once the distal end of the device 10 is properly positioned within a body cavity for the intended procedure, and then maintaining the positions of the legs 14 within the body cavity while the sheath 12 is advanced over the legs 14 to collapse them. A distal portion 16 of the cable 18 projects from the sheath 12 so as to be surrounded by the legs 14, as seen in FIGS. 1, 3 and 4. The sheath 12 can be formed of any suitable material known in the art. The passage within the sheath 12 can be sized to be sufficiently large to not only accommodate the legs 14 and cable 18, but also provide an irrigation or injection lumen, or a channel for a laser fiber to be passed through so that stones and other biological materials can be captured, held and fragmented to allow the resulting fragments to pass. The sheath 12 may also be equipped with a hollow channel (not shown) through which a sparking wire can be passed to enable the legs 14 (if formed of a conductive material) to be energized with electrosurgical cutting or coagulating current.

The embodiment of FIGS. 1 through 4 shows the ends 28 of the legs 14 as being connected together, so that the legs 14 in combination form a basket 20. In FIGS. 1 through 4, the ends 28 of the legs 14 and the distal portion 16 of the cable 18 are interconnected with a distal connector 30 which, depending on the materials used to form the legs 14 and cable 18, can be attached by metallurgical joining (e.g., soldering, brazing, etc.) or with a mechanical crimp joint. While the device 10 is shown as being equipped with four legs 14, it is foreseeable that fewer or greater numbers of legs could be employed. For example, the device could have two legs 14 (forming, in effect, a snare) or as many as eight legs 14 or more. As represented in FIG. 1, the legs 14 are formed to have a parabolic curved shape, as by such known methods as stamping, rolling, extruding, etc. The legs 14 are formed from a sufficiently rigid material, such as a stainless steel, or a "shape memory" nickel-titanium alloy such as NITINOL, so that the parabolic curved shape of the legs 14 causes the midportions of the legs 14 to automatically deploy radially outward and away from each other (and away from the distal portion 16 of the cable 18) when the legs 14 are deployed outside the sheath 12 with the cable 18. As a result, the device 10 does not require a plunger capable of being actuated relative to the legs 14 in order to force the legs 14 radially apart to form the basket 20 of FIG. 1. The legs 14 are sufficiently elastically deformable so that, when the sheath 12 is advanced over the legs 14, the legs 14 elastically collapse radially toward each other to acquire an intermediate position (FIG. 3) in which the basket 20 is partially collapsed. With further advancement of the sheath 12 (FIG. 4), the legs 14 are largely stowed within the sheath 12 and substantially parallel to each other and to the distal portion 16 of the cable 18.

A key feature of the present invention is that each leg 14 has a concave-convex cross-section that contributes greater strength to the legs 14, such that the legs 14 maintain their form and alignment and provide greater grasping strength and expansion force than extraction devices equipped with wires having other cross-sectional shapes. As a result, the device 10 is well suited for moving, manipulating and extracting biological material, such as calculi, stones, etc. As depicted in FIG. 5, the legs 14 have a concave-convex cross-section in the sense that the inward surfaces 22 of the legs 14 facing each other are concave, while the oppositely-disposed outward surfaces 24 of the legs 14 are convex. Each surface 22 and 24 is represented in FIG. 5 as having a substantially constant radius of curvature, with the result that thicknesses of the legs 14 in the direction of a radial of the curvature are substantially constant. The sides 26 of the legs 14 are contiguous with the surfaces 22 and 24, and can be of any suitable shape, e.g., rounded, flat such as the radials of the curvatures of the surfaces 22 and 24, etc. When fully collapsed, the legs 14 define a tubular shape in the sense that the legs 14 in combination define a circular exterior cross-section and a circular opening that is sized to accommodate the cable 18. As such, and also as evident from FIG. 4, the sides 26 of the legs 14 contact each other when the legs 14 are fully collapsed within the sheath 12. This aspect of the invention, in which gaps between adjacent legs 14 are eliminated as the sheath 12 advances over the legs 14, enables the device 10 to define a circumferentially continuous enclosure capable of fully containing small renal and ureteral calculi and other very small biological material. This aspect of the invention also enables the device 10 to be used to remove polyps or growths for biopsy by placing the basket 20 so that the polyp/growth is between a pair of adjacent legs 14, after which the basket 20 is completely collapsed with the sheath 12 such that the sides of the legs 14 have a scissor effect on the polyp/growth.

FIG. 6 shows a second embodiment of an extraction device 110 of this invention, in which the legs 14 have a longitudinal configuration that causes the basket 120 to have a helical shape. Other than the helical shape of the basket 120, the device 110 can have an identical construction to the device 10 of FIGS. 1 through 4.

When used to remove a stone (or calculi or other object) from a cavity of the human body, the legs 14 are extended from the sheath 12 with the cable 18 such that the legs 14 resiliently expand outward to reacquire their parabolic curved shape. Once the stone is surrounded by the legs 14 so as to be nested with the basket 20, the cable 18 is actuated relative to the sheath 12 to advance the sheath 12 over the legs 14, causing the basket 20 to collapse and grasp the stone. By subsequently extending the legs 14 from the sheath 12, the stone can be released. As such, surgically moving, manipulating and extracting bodies and materials within the human body is performed without additionally operating a plunger or other extraneous component to expand and contract the basket 20 formed by the legs 14.

Figure 7:
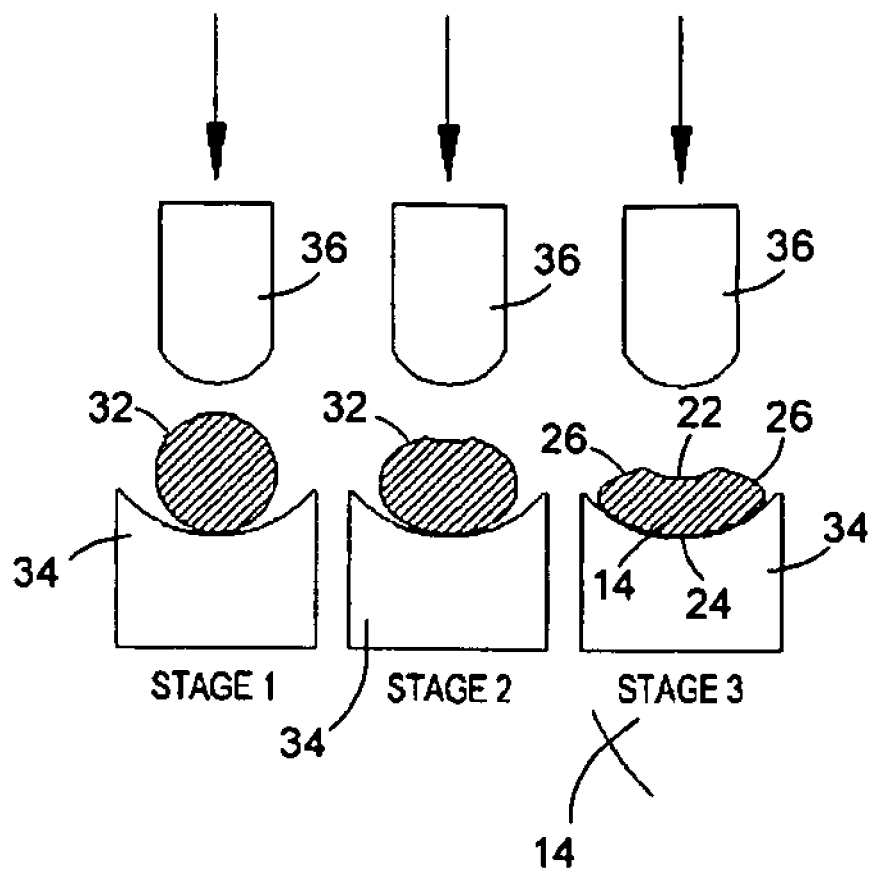
FIG. 7 depicts a multistage process for producing legs for devices in accordance with the present invention.

As noted above, the legs 14 can be formed by such known methods as stamping, rolling, extruding, etc. Rolling and stamping are particularly desirable from the standpoint of being able to produce legs 14 that are dense and therefore capable of generating greater strength and expansion force. FIG. 7 depicts a multistage stamping or rolling process suitable for producing the legs 14 for the devices of FIGS. 1 through 6, as well as subsequent embodiments of the invention described in reference to FIGS. 9 through 12. In FIG. 7, a solid round wire 32 is shown supported on a die (or bottom roller) 34, and then engaged with a ram (or upper roller) 36 during multiple operations until a leg 14 is produced. Legs 14 produced in this manner can be continuous and spooled in coils for later cutting to length and assembly with the cable 18. As a result of being formed from round solid wire 32, the lateral sides 26 of the leg 14 are not as flat as those of the leg 14 depicted in FIG. 5, and the edges defined at the intersections of the lateral sides 26 with the concave inward surface 22 and the convex outward surface 24 of the leg 14 are rounded and not sharp. Furthermore, the inward and outward surfaces 22 and 24 are not necessarily equidistant from each other, resulting in the leg 14 having a nonuniform radial thickness. For example, the leg 14 in FIG. 7 can be seen to be thinner near its sides 26 than at its center.

Figure 8:
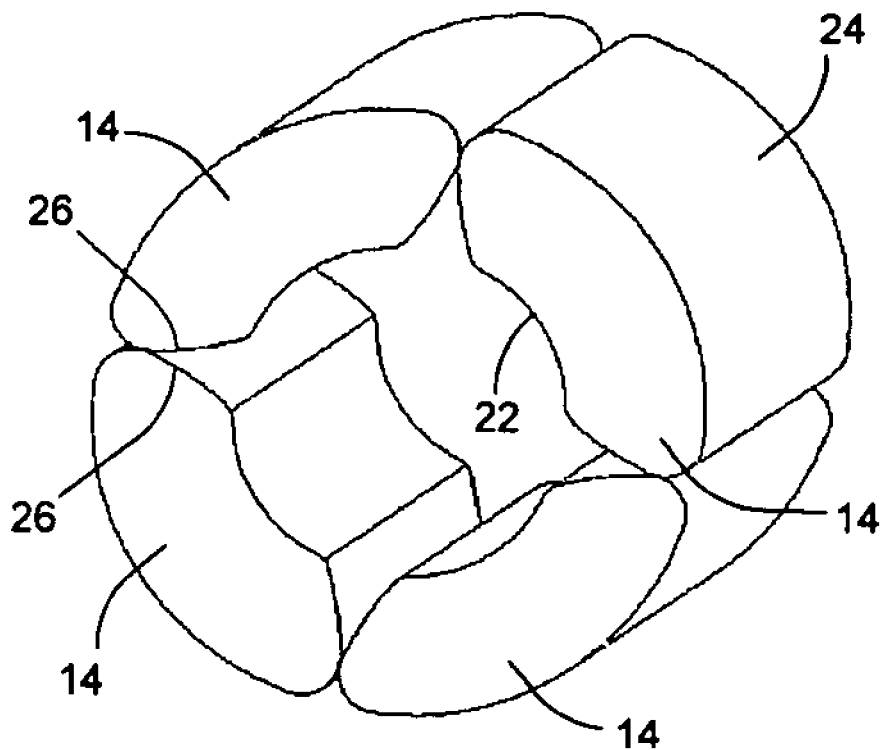
FIG. 8 is a perspective view of distal ends of legs produced by the process depicted in FIG. 7 and in a fully collapsed position.

As previously described in reference to the embodiment of FIGS. 1 through 4, when fully collapsed the legs 14 define a tubular shape in the sense that the legs 14 in combination define a circular exterior cross-section and a circular opening, which is a result of their lateral sides 26 contacting each other along their entire lengths. The tubular shape defined by the legs 14 is depicted in FIG. 8, which evidences that gaps between adjacent legs 14 are eliminated so that the legs 14 define a circumferentially continuous enclosure capable of fully containing very small biological material. This aspect of the invention also maximizes the grasping strength of the legs 14 when attempting to capture an object.

Figure 9:
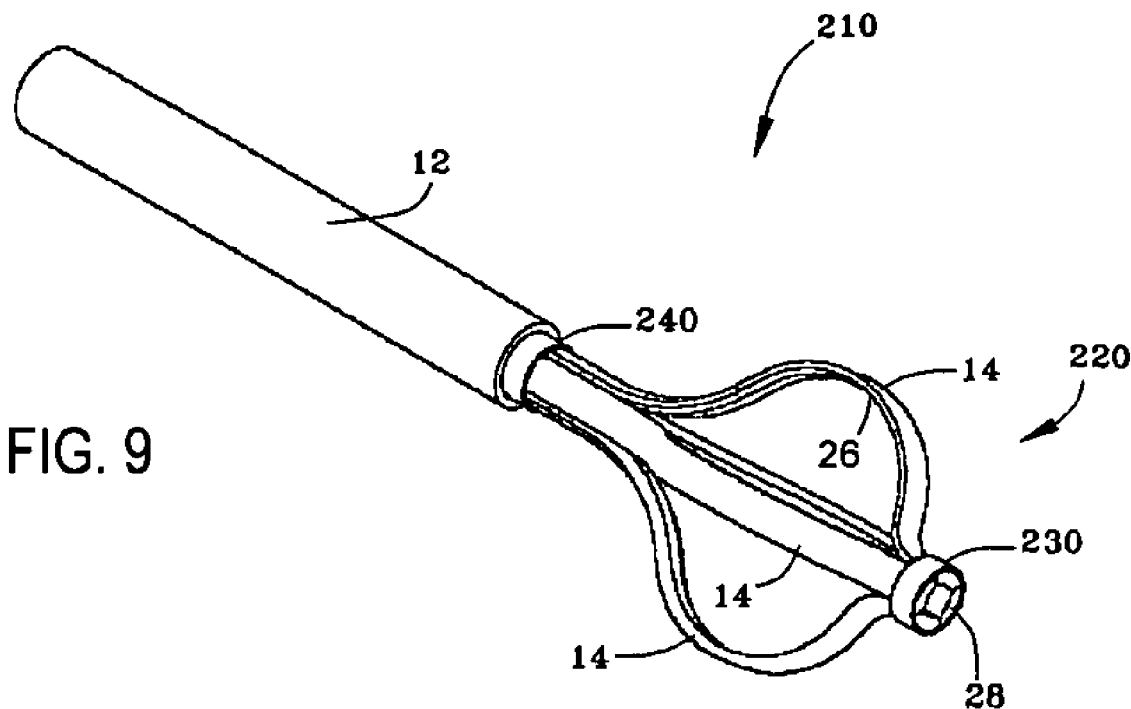
FIGS. 9 and 10 are perspective views of a surgical device in deployed and stowed positions, respectively, in accordance with a third embodiment of this invention.
Figure 10:
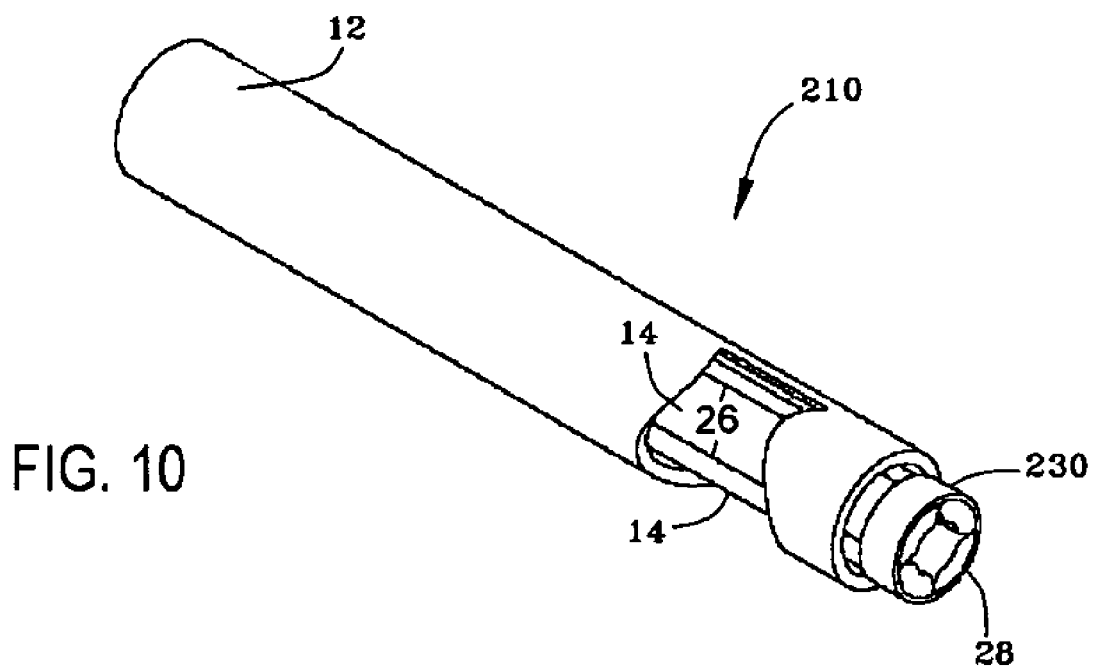

FIGS. 9 and 10 represent an extraction device 210 with legs 14 shaped as a result of being produced by the process depicted in FIG. 7. As with the previous embodiments, the legs 14 are adapted for being stowed within a sheath 12, where the legs 14 assume a fully-collapsed position consistent with FIG. 4. As before, the legs 14 may be actuated with a cable (not shown) or other suitable actuating member capable of simultaneously retracting the legs 14 into the sheath 12 and deploying the legs 14 from the sheath 12. In the embodiment of FIGS. 9 and 10, the proximal ends of the legs 14 are connected together with a proximal connector 240 while the distal ends 28 of the legs 14 are connected together with a distal connector 230 so that the legs 14 in combination form a basket 220 when deployed. FIG. 10 is illustrated with a portion of the sheath 12 removed to expose the collapsed legs 14 within the sheath 12 and evidence contact between the lateral sides 26 of the legs 14. As evident from FIGS. 9 and 10, the ability to fully collapse the legs 14 until their sides 26 touch enables the device 210 to fully contain small renal and ureteral calculi. This aspect of the invention also enables the device 210 to be used to remove polyps or growths for biopsy by placing the basket 220 so that the polyp/growth is between a pair of adjacent legs 14, after which the basket 220 is completely collapsed with the sheath 12 such that the sides 26 of the legs 14 have a scissor effect on the polyp/growth. Though not depicted in FIGS. 9 and 10, the device 210 could be configured with the cable 18 of FIGS. 1 through 4 extending from the sheath 12 alongside the legs 14, with the distal ends 28 of the legs 14 attached to the distal end 16 of the cable 18 with the distal connector 230 or other suitable means, as discussed in reference to the embodiment of FIGS. 1 and 4.

Figure 11:
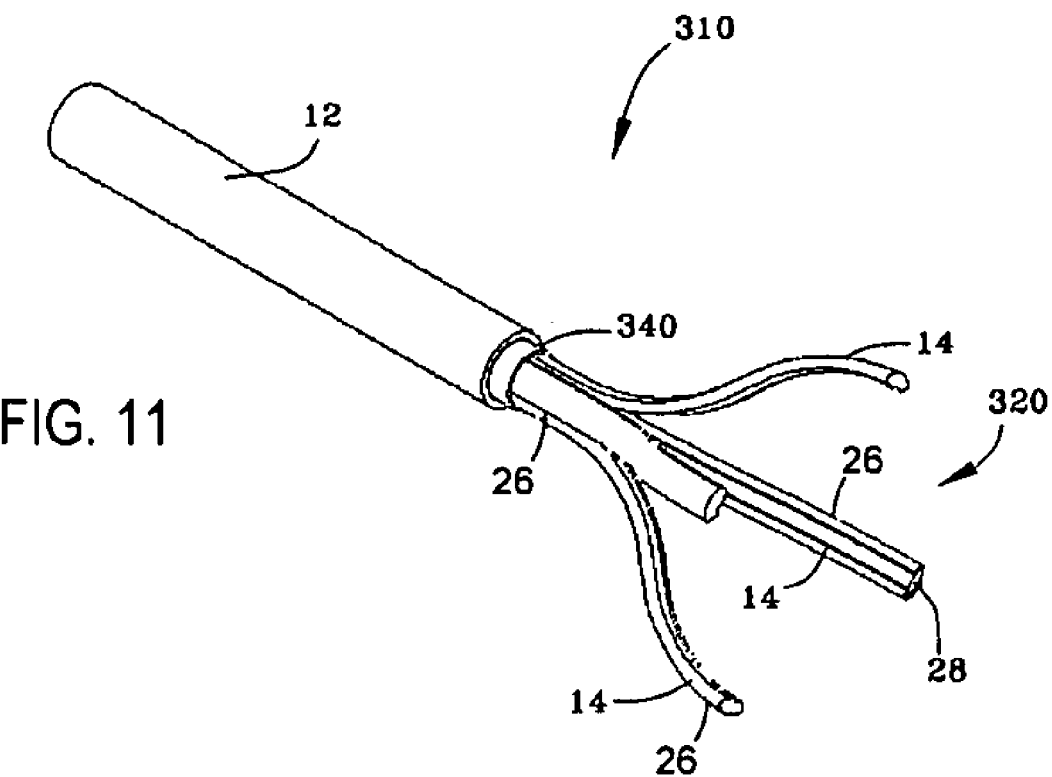
FIGS. 11 and 12 are perspective views of a surgical device in deployed and stowed positions, respectively, in accordance with a fourth embodiment of this invention.
Figure 12:
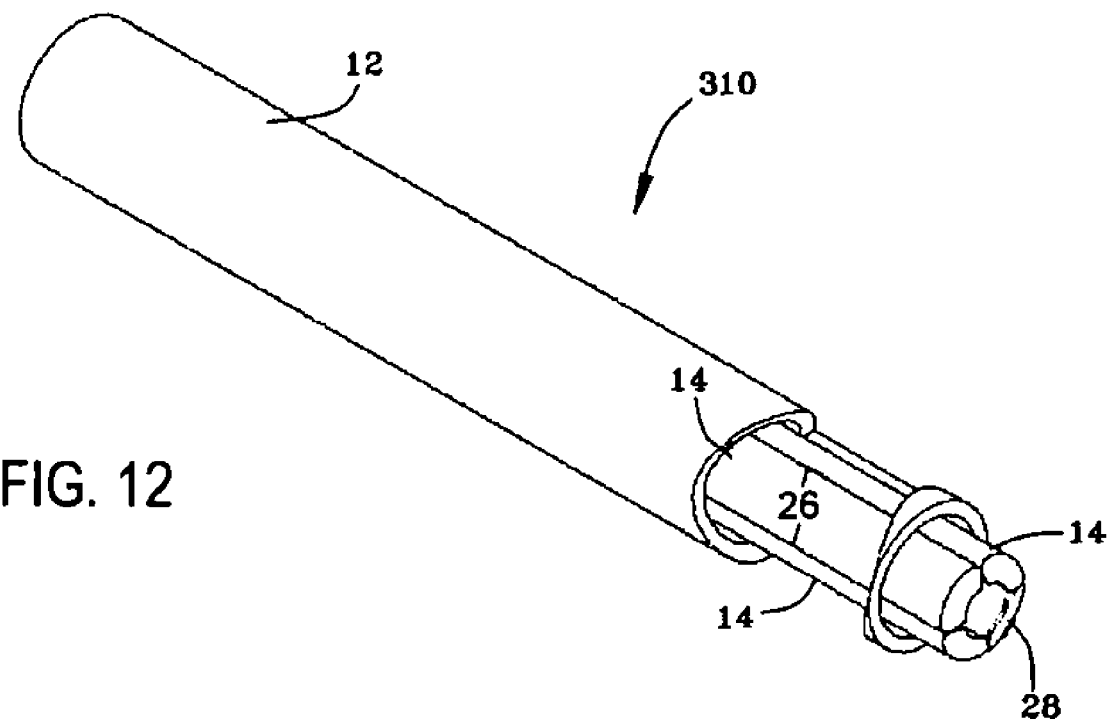

An extraction device 310 represented in FIGS. 11 and 12 is essentially identical to that of FIGS. 9 and 10, with the exception that a distal connector is not employed such that the device 310 operates as forceps 320. As in the embodiment of FIGS. 9 and 10, the proximal ends of the legs 14 are connected together with a proximal connector 340, and a portion of the sheath 12 is removed in FIG. 12 to illustrate the collapsed legs 14 within the sheath 12. Also consistent with the previous embodiments of this invention, the ability of the device 310 to fully collapse the legs 14 until their sides 26 touch enables the device 210 to fully contain small renal and ureteral calculi, as well as have a scissor effect to remove polyps and other growths. The embodiment of FIGS. 11 and 12 provides the additional capability of grasping biological materials with the distal ends 28 of the legs 14, which together define and operate as jaws capable of extracting materials embedded in a cavity wall. The terminal surfaces of the distal ends 28 can be angled outward in the distal direction so that embedded materials, such as a stone embedded in the wall of the calyces in a kidney, can be more readily extracted.

While the invention has been described in terms of a preferred embodiment, it is apparent that other forms could be adopted by one skilled in the art. For example, appropriate materials could be substituted for those noted. Accordingly, the scope of the invention is to be limited only by the following claims.

What is claimed:

1. A surgical device having a sheath with an interior passage and legs slidably received within the passage of the sheath, the legs being adapted to move outwardly away from each other in a radially outward direction when deployed from the sheath to establish a deployed position, and to move inwardly toward each other in a radially inward direction to collapse within the sheath and define a stowed position, each of the legs having a transverse cross-sectional shape defined by a transverse cross-section through the leg and through a radially-inward first surface thereof that is concave, an oppositely-disposed radially-outward second surface thereof that is convex, and two oppositely-disposed lateral sides thereof interconnecting the first and second surfaces, each of the lateral sides defining with the first and second surfaces a rounded radially-inward first edge and a rounded radially-outward second edge, respectively, the lateral sides of adjacent pairs of the legs having portions that do not contact each other when the legs are in the deployed position, the legs and sheath being configured to cause the legs to fully collapse within the sheath such that the portions of the lateral sides of adjacent pairs of the legs contact each other at only the second edges of the legs when the legs are in the stowed Position within the sheath to thereby define a tubular shape comprising a circumferentially continuous enclosure surrounding an opening.

2. The surgical device according to claim 1, wherein each leg has a parabolic curved shape which causes the legs to automatically move radially outward and away from each other when deployed outside the sheath without the assistance of a second component to engage and force the legs away from each other.

3. The surgical device according to claim 1, wherein the legs have adjacent distal ends that are connected together so that the legs define a basket in the deployed position and the basket collapses as the legs are retracted into the sheath so as to define a grasping position in which the legs are operable to perform a grasping operation.

4. The surgical device according to claim 1, wherein the legs have adjacent distal ends that are not connected together so that the legs define forceps in the deployed position and the forceps collapse as the legs are retracted into the sheath so as to define a grasping position.

5. The surgical device according to claim 1, wherein the device has more than two of the legs and the first surfaces of the legs face each other.

6. The surgical device according to claim 1, wherein the device is a surgical instrument chosen from the group consisting of urological, gynecological, cardiological, laparoscopical and gastro-intestinal instruments.

7. A surgical extraction device having a sheath with an interior passage, at least three legs that project from the passage of the sheath, and actuating means for deploying the legs from the sheath and for retracting the legs into the sheath, each of the legs comprising a transverse cross-sectional shape defined by a transverse cross-section through the leg and through a radially-inward concave surface thereof, a radially-outward convex surface thereof oppositely disposed from the concave surface, and lateral sides thereof oppositely disposed from each other and interconnecting the first and second surfaces, each of the lateral sides defining with the concave and convex surfaces a rounded radially-inward first edge and a rounded radially-outward second edge, respectively;

wherein the concave surfaces of the legs face each other, the legs move outwardly away from each other in a radially outward direction when deployed from the sheath by the actuating means to establish a deployed position, and the legs are forced to move inwardly toward each other in a radially inward direction when retracted into the sheath by the actuating means to establish a grasping position in which the legs are fully collapsed with the lateral sides of adjacent pairs of the legs contacting each other at only the second edges of the legs to thereby define a tubular shape comprising a circumferentially continuous enclosure surrounding an opening.

8. The surgical extraction device according to claim 7, wherein each leg has a parabolic curved shape which causes the legs to automatically move radially outward and away from each other when deployed outside the sheath without the assistance of a second component to engage and force the legs away from each other.

9. The surgical extraction device according to claim 7, wherein the legs have adjacent distal ends that are connected together so that the legs define a basket in the deployed position and the basket collapses as the legs are retracted into the sheath by the actuating means so as to establish the grasping position.

10. The surgical extraction device according to claim 7, wherein the legs have adjacent distal ends that are not connected together so that the legs define forceps in the deployed position and the forceps collapse as the legs are retracted into the sheath by the actuating means so as to establish the grasping position.

11. The surgical extraction device according to claim 7, wherein the inward and outward surfaces of each leg are not equidistant from each other such that each leg has a nonuniform radial thickness.

12. The surgical extraction device according to claim 7, wherein the device is chosen from the group consisting of urological instruments, gynecological instruments, cardiological instruments, laparoscopical instruments, and gastro-intestinal instruments.

* * * * *